(12) United States Patent
Hu et al.

(10) Patent No.: US 11,732,231 B2
(45) Date of Patent: Aug. 22, 2023

(54) COMPOSITE MEMBRANE AND MANUFACTURING METHOD THEREOF

(71) Applicant: National Central University, Taoyuan (TW)

(72) Inventors: Wei-Wen Hu, Taoyuan (TW); Chia-Wen Tsao, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 415 days.

(21) Appl. No.: 17/076,912

(22) Filed: Oct. 22, 2020

(65) Prior Publication Data

US 2022/0089990 A1   Mar. 24, 2022

(30) Foreign Application Priority Data

Sep. 24, 2020   (TW) .................................. 109133088

(51) Int. Cl.

| | |
|---|---|
| *C08F 2/46* | (2006.01) |
| *C08F 2/50* | (2006.01) |
| *C08G 61/04* | (2006.01) |
| *C12M 1/12* | (2006.01) |
| *C12M 1/00* | (2006.01) |
| *C12M 1/42* | (2006.01) |
| *C12N 5/071* | (2010.01) |
| *C12M 3/00* | (2006.01) |
| *C09D 4/00* | (2006.01) |
| *C12M 1/26* | (2006.01) |
| *C12N 5/00* | (2006.01) |

(52) U.S. Cl.
CPC .............. *C12M 25/02* (2013.01); *C09D 4/00* (2013.01); *C12M 21/08* (2013.01); *C12M 23/20* (2013.01); *C12M 23/26* (2013.01); *C12M 33/14* (2013.01); *C12M 35/02* (2013.01); *C12M 35/04* (2013.01); *C12N 5/0068* (2013.01); *C12N 5/0697* (2013.01); *C12N 2527/00* (2013.01); *C12N 2533/30* (2013.01); *C12N 2539/10* (2013.01)

(58) Field of Classification Search
CPC ...... C12M 33/14; C12M 25/02; C12M 35/04; C12M 35/02; C12M 23/20; C12M 23/26; C12M 21/08; C09D 4/00; C12N 5/0697; C12N 5/0068; C12N 2539/10; C12N 2533/30; C12N 2527/00; C08F 226/00; C08F 220/54
USPC .......................... 522/175, 174, 173, 1; 520/1
See application file for complete search history.

(56) References Cited

U.S. PATENT DOCUMENTS

2016/0312387 A1\*   10/2016   Zhang ............... C04B 35/62855

\* cited by examiner

*Primary Examiner* — Jessica Whiteley
(74) *Attorney, Agent, or Firm* — Demian K. Jackson; Jackson IPG PLLC (57) ABSTRACT

The present invention relates to a composite membrane. The composite membrane includes: an elastic polymer substrate having a first surface processed by a surface modification; and a thermosensitive conductive layer formed on the first surface by performing a co-polymerization process, allowing an electrical current to pass through, and altering a hydrophilicity of a membrane surface in response to a change of a temperature.

4 Claims, 8 Drawing Sheets

COMPOSITE MEMBRANE AND MANUFACTURING METHOD THEREOF

CROSS-REFERENCE TO RELATED APPLICATION

This application claims priority benefit to Taiwan Invention Patent Application Serial No. 109133088, filed on Sep. 24, 2020, in Taiwan Intellectual Property Office, the entire disclosures of which are incorporated by reference herein.

FIELD

The present invention relates to a composite membrane which has multiple physical properties of the high stretchability, the conductivity and the thermosensitivity at the same time, and a manufacturing method thereof.

BACKGROUND

The tissue engineering is the technology of engineering to promote the repair of damaged tissues. A common strategy in the field of the tissue engineering is to provide appropriate induction to guide stem cells differentiate in vitro, and to eventually create functional tissues.

In addition to the chemical stimulation and biological signal stimulation, the usage of physical stimulation to provide a biomimic environment is extremely important as well. The development of the bioreactor is aimed to provide appropriate physical stimulations, such as electrical stimulation or mechanical stimulation, to cells.

In the conventional technique, in order to harvest the cells from the bioreactor after stimulation, enzymes are commonly used to digest the extracellular matrix (ECM) around the cells, so that the cells can be detached from the substrate of the bioreactor. However, the conventional technique has the problem that the cultivated and stimulated tissue formed on the bioreactor has a specific and ordered structure, which is extremely important for the function of the tissue, and if the tissue is decomposed into individual cells, the ordered structure disappears; furthermore, the cells environment, such as adjacent cells and extracellular matrix, has a decisive influence on cell physiology. As a result, the cells harvested by enzyme may have dysfunction because of being unable to receive the signals from the original surrounding cells and extracellular matrix.

The cell sheet engineering refers to the removal of the cultured cell sheet from the substrate, and try to retain the ECM and connections between cells, so as to improve viability of the cells. The retained connections between cells of cell sheet is particular important for the tissue's function, for example, the electrical signals generated by cardiac myoblasts to induce heart beating is transmitted through the connections between cardiac myoblasts.

In the state of the art, there are many methods for harvesting cell sheets, and the most-commonly known method is to coat a thermoresponsive polymer layer onto the substrate to which the cells are attached. When temperature is higher than 32° C., the thermoresponsive polymer chain is in hydrophobic entanglement which is suitable for cell attachment. When the temperature drops below 32° C., the thermoresponsive polymer chains demonstrate hydrophilic stretch straight-chain conformation, so that the extracellular matrix is pushed away and the cells can be removed from the surface.

Although thermosensitive materials have been developed for cell sheet harvesting, they are applicable for the case of simple tissue culture only. However, it is still a huge challenge to provide combined bio-stimulation during the culture process, remove the intact cell sheet after stimulation, and then apply the cell sheet for subsequent applications. So far, there are still few related technologies.

Therefore, it is necessary to develop a suite of equipment or a method capable of applying mechanical and electrical stimulations to cells at the same time, and preserving the connections between the cells and the integrity of extracellular matrix during cell harvesting. Consequently, the inventors develop a composite membrane and a manufacturing method thereof according to tests and research, to solve the above-mentioned issues.

SUMMARY

The present invention proposes to combine thermosensitive polymer monomers, such as N-isopropylacrylamide (NIPAAm), and conductive polymer monomers, such as pyrrole (Py) for copolymerization, and deposit the copolymer on the surface of an elastic polymer substrate, such as polydimethylsiloxane (PDMS), so as to obtain a composite membrane of P(Py-co-NIPAAm)/PDMS. The composite membrane has excellent stretchability and also has conductivity and thermosensitivity, and can be used to completely remove the required cell sheet by a cooling and detaching process. The cell sheet obtained by the cooling and detaching process has a high viability and a large amount of extracellular matrices are completely retained.

The composite membrane manufactured by the manufacturing method in accordance with the present invention can be applied to various bio-stimulation devices for culturing and differentiating stem cells to obtain functional tissues. The operators can freely select and combine various parameters to perform combined stimulations to the cultured cells; for example, the combined stimulations include mechanical stimulation, electrical stimulation or a combination thereof.

The present invention provides a composite membrane. The membrane includes an elastic polymer substrate having a first surface processed by a surface modification; and a thermosensitive conductive layer formed on the first surface by performing a co-polymerization process, allowing an electrical current to pass through, and altering a hydrophilicity of a membrane surface in response to a change of a temperature.

The present invention provides a composite membrane manufacturing method. The method includes steps of providing an elastic polymer substrate having a first surface; processing the first surface by a surface modification; and copolymerizing a plurality of monomers of conductive polymer and a plurality of monomers of thermosensitive polymer to form a thermosensitive conductive layer on the first surface, wherein the thermosensitive conductive layer allows an electrical current to pass through, and alters a hydrophilicity of a membrane surface in response to a change of a temperature.

The above content described in the summary is intended to provide a simplified summary for the presently disclosed invention, so that readers are able to have an initial and basic understanding to the presently disclosed invention. The above content is not aimed to reveal or disclose a comprehensive and detailed description for the present invention, and is never intended to indicate essential elements in various embodiments of the present invention, or define the scope or coverage of the present invention.

DESCRIPTION OF THE DRAWINGS

A more complete appreciation of the invention and many of the attendant advantages thereof are readily obtained as the same become better understood by reference to the following detailed description when considered in connection with the accompanying drawing, wherein.

DETAILED DESCRIPTION

The present disclosure will be described with respect to particular embodiments and with reference to certain drawings, but the disclosure is not limited thereto but is only limited by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice.

It is to be noticed that the term "including", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device including means A and B" should not be limited to devices consisting only of components A and B.

The disclosure will now be described by a detailed description of several embodiments. It is clear that other embodiments can be configured according to the knowledge of persons skilled in the art without departing from the true technical teaching of the present disclosure, the claimed disclosure being limited only by the terms of the appended claims.

Figure 1:
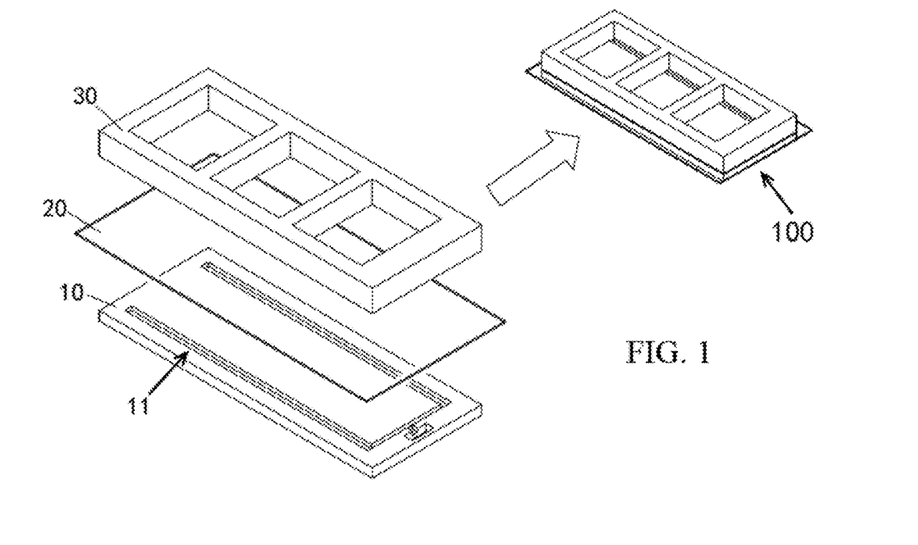
FIG. 1 is a schematic diagram illustrating the structure of a cell stimulation device using the composite membrane in accordance with the present invention.

FIG. 1 is a schematic diagram illustrating the structure of a cell stimulation device using the composite membrane in accordance with the present invention. Preferably, the composite membrane proposed in the present invention can be used as a culture membrane 20 of the cell stimulation device 100 capable of providing bio-stimulation. The cell stimulation device 100 preferably includes a flow layer 10, the culture membrane 20 and a culture layer 30. The flow layer 10, the culture membrane 20 and the culture layer 30 are preferably combined by PDMS. The flow layer 10 is configured with multiple channels 11. The composite membrane proposed in the present invention is preferably applied as the culture membrane 20.

Figure 2:
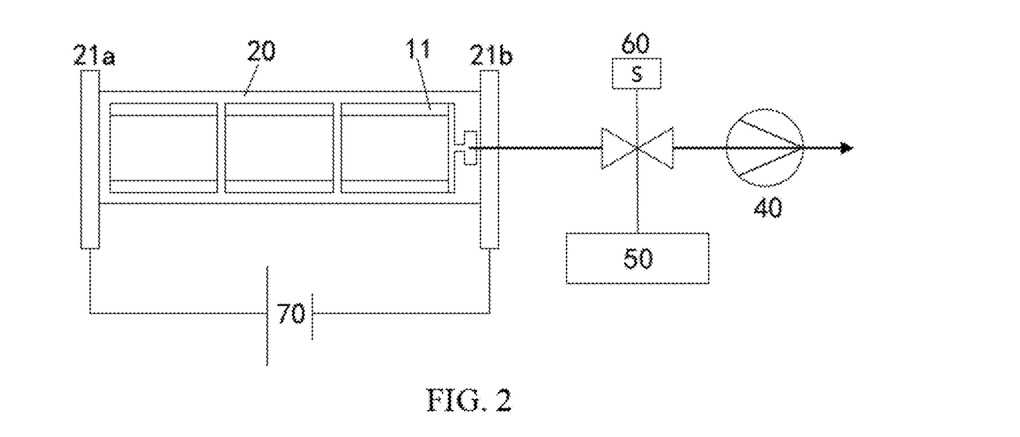
FIG. 2 is a schematic diagram illustrating the operation of the cell stimulation device using the composite membrane in accordance with the present invention.

FIG. 2 is a schematic diagram illustrating the operation of the cell stimulation device using the composite membrane in accordance with the present invention. As shown in FIG. 2, a pair of electrodes 21a and 21b are arranged on two ends of the culture membrane 20, and configured to receive a voltage difference supplied from a power supply 70, to pass electrical current through the culture membrane 20. After the flow layer 10 and the culture membrane 20 are combined, a fluid pump 40 can be used to pump out gas or fluid from the flow layer 10, so as to create a negative pressure to generate suction to draw the culture membrane 20 into the channel 11, thereby stretching the culture membrane 20 to provide mechanical and electrical stimulation to the cultured cells. A timer relay 50 controls the switching operation of an electromagnetic valve 60 to determine the magnitude and on-off timing of the negative pressure generated by the fluid pump 40, so as to control the strains and the repeating frequency of the culture membrane 20.

The elastic polymer substrate included in the composite membrane in accordance with the present invention is preferably made based on the following steps: (1) smoothing the elastic polymer solution; (2) curing the smoothed elastic polymer solution; (3) removing the cured elastic polymer, so as to complete the preparation of elastic polymer substrate.

For example, in an embodiment, the above steps can include: (1) blending the A and B agents of PDMS in a weight ratio of 10:1, and uniformly stirring the mixture, wherein the weight of the mixed A and B agents is about 3 g per sheet; (2) pouring the viscous liquid PDMS material on a flat surface, and using a coating scraper or a spin coater to form a membrane and adjust the thickness of the membrane, wherein the thickness is 200 μm preferably; (3) placing the membrane-like liquid PDMS into an oven; (4) baking the membrane-like PDMS at 85° C. for 6 hours; (5) carefully removing the cured PDMS membrane, so as to complete the preparation of elastic substrate.

Figure 3A:
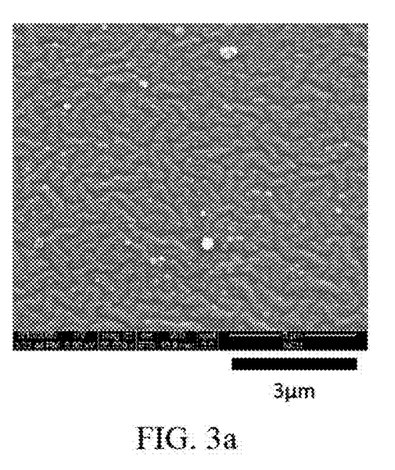
FIGS. 3a and 3b are images showing multiple wrinkled and corrugated structures formed through etching effect resulted from the alkaline aqueous solution immersion to improve surface roughness of the elastic polymer substrate in accordance with the present invention.
Figure 3B:
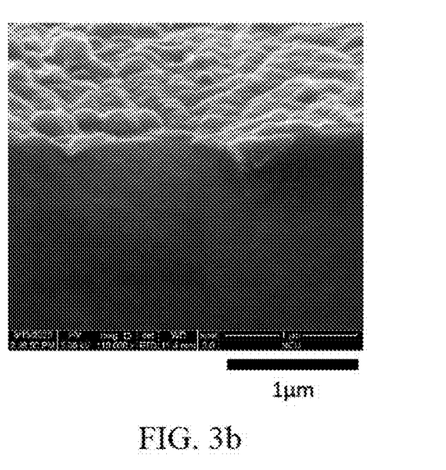

Subsequently, the prepared PDMS membrane is further processed by a chemical surface modification, and the process can be achieved by implementing the following steps: (1) immersing the PDMS membrane into acidic aqueous solution or alkaline aqueous solution with specific molar concentration at room temperature for about 5 to 7 hours, preferably 6 hours; (2) removing the aqueous solution for the surface modification; (3) washing the processed PDMS membrane with DI water, wherein the surface of the PDMS membrane has multiple wrinkled structures, corrugated structures and micro pores that are formed by etching effect resulted from the surface modification, as shown in FIGS. 3a and 3b, so as to improve surface roughness and stretchability of the PDMS membrane. Furthermore, the wrinkled structures and corrugated structures are distributed substantively uniformly, so that the light passing through PDMS membrane can be reflected and refracted substantively regularly, and it facilitates subsequent imaging and renders the PDMS membrane to have excellent optical properties.

For example, in an embodiment, the above steps can include: (1) immersing and still placing the PDMS membrane in NaOH aqueous solution with equivalent concentration of 3N for etching process at room temperature for 6 hours; (2) removing the NaOH aqueous solution; (3) repeatedly washing the surface of the processed PDMS membrane by DI Water to remove residual NaOH aqueous solution.

Then, a thermosensitive conductive layer is deposited on the unilateral surface of the modified PDMS membrane by implementing co-polymerization process. The above-process can be implemented through the following steps: (1) placing the modified elastic polymer membrane flat on, for example but not limited to, a surface a petri dish; (2) preparing initiator solution including an initiator in solvent, conductive polymer monomeric solution including the plurality of monomers of conductive polymer in solvent, and a thermosensitive polymer monomeric solution including the plurality of monomers of thermosensitive polymer in solvent, wherein the three solutions are with specific molar concentrations; (3) blending the conductive polymer monomeric solution and the thermosensitive polymer monomeric solution, and then adding a specific amount of catalyst solution, and then pouring the mixture into the petri dish and blending the mixture uniformly; (4) adding the initiator solution into the mixture and blending the mixture uniformly, and placing the mixture at room temperature for a period of time, to deposit a thermosensitive conductive layer on the PDMS membrane, so as to form the composite elastic thermosensitive conductive membrane; (5) removing the solution from the petri dish, and repeatedly washing the newly formed composite membrane with deionized water; (6) placing the composite membrane in an oven to dry at a specific temperature for a period of time; (7) removing the powdery substance remained on the surface of the dried composite membrane, so as to complete the production of composite membrane.

Figure 4:
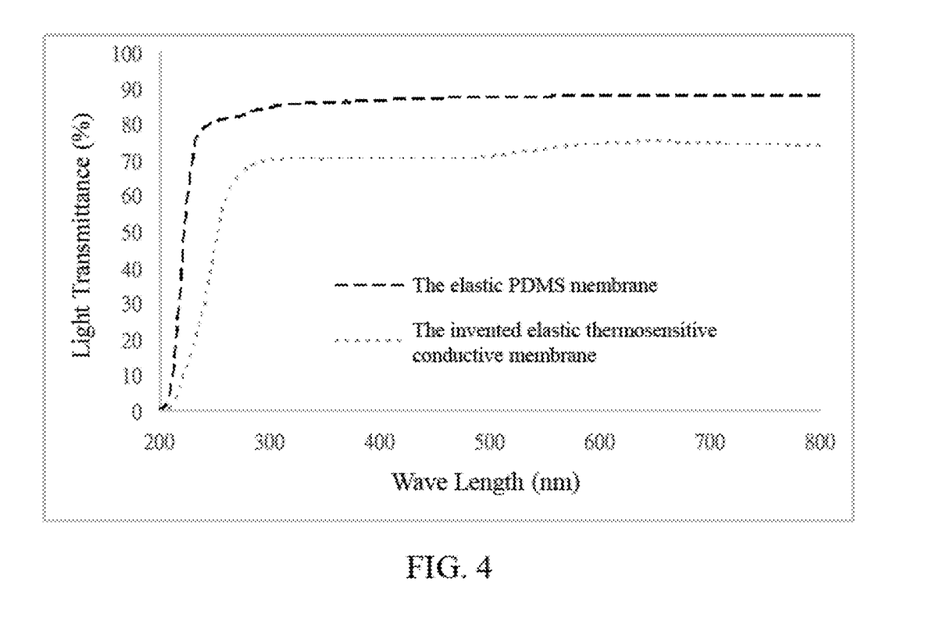
FIG. 4 is a line graph showing respective light transmittances of the elastic polymer membrane and the elastic thermosensitive conductive membrane with respect to different wave length in accordance with the present.

For example, in an embodiment, the above steps include that the copolymerization of the thermosensitive polymer monomer of NIPAAm and the conductive polymer monomer of Py are copolymerized to form the thermosensitive conductive layer of P(Py-co-NIPAAm) on the unilateral surface of the PDMS membrane. The above process include: (1) placing the modified PDMS membrane flat on the surface of a petri dish with a diameter of about 15 cm; (2) preparing 15 ml of ammonium persulfate (APS) initiator solution with 0.2M molar concentration, 7.5 ml of conductive polymer monomeric solution including monomers of Py with 2.0M molar concentration, and 7.5 ml of thermosensitive polymer monomeric solution including monomers of NIPAAm with 1.32M molar concentration at room temperature; (3) blending the conductive polymer monomeric solution including monomers of Py and the thermosensitive polymer monomeric solution including monomers of NIPAAm at room temperature, and then adding 166 μl of N,N,N',N'-tetramethyl-ethane-1,2-diamine (TEMED) catalyst solution into the mixture, and pouring the mixture into a petri dish, and using a vortex mixer to uniformly shake and blending the mixture; (4) adding the APS initiator solution into the mixture and blending the mixture uniformly, and placing the mixture to react at room temperature for about 1 hour, to form a thermosensitive conductive layer of P(Py-co-NIPAAm) on the PDMS membrane; (5) removing the solution from the petri dish, and repeatedly cleaning the P(Py-co-NIPAAm)/PDMS membrane with DI water; (6) placing the P(Py-co-NIPAAm)/PDMS membrane in an oven to dry at 45° C. for a period of time; (7) wiping the surface of dried composite membrane with a fine fiber cloth to remove the powdery substance remained on the surface of the composite membrane, so as to complete the production of composite elastic thermosensitive conductive membrane. The prepared elastic thermosensitive conductive membrane has appearance in light black but a light transmittance in range of 60% up to 70%, because the thickness of the thermosensitive conductive layer is extremely thin, as shown in FIG. 4.

The composite membrane proposed in the present invention has the surface layer processed by the chemical surface modification in advance, and according to the water contact angle detection result, the modified PDMS membrane has obviously smaller contact angle, so that hydrophilic tendency of the surface layer of the PDMS membrane is improved, and it is helpful for monomers of Py and NIPAAm to diffuse into the micro pores formed on the surface layer, and the monomers of Py and NIPAAm in the micro pores can perform the co-polymerization process through APS, to physically entangle with part of the polymer chains of PDMS and promote Py or NIPAAm to deposit and co-polymerize on the surface of PDMS membrane, so as the thermosensitive conductive layer of P(Py-co-NIPAAm) can be tightly combined with the PDMS membrane.

In order to completely remove and obtain the stimulated cell tissue, the present invention proposes that the conductive polymer monomer of Py and thermosensitive polymer monomers of NIPAAm are copolymerized in the PDMS elastic polymer substrate to obtain the P(Py-co-NIPAAm)/PDMS membrane with excellent stretchability, conductivity and thermosensitivity. The molecular chain of the thermosensitive conductive layer can alert the hydrophobicity of the surface layer in responsive to a change of temperature. When the temperature increases, the molecular chain of the thermosensitive conductive layer tends to form a hydrophobic entanglement flat conformation, to which is easier for cell to attach. When the temperature decreases, the molecular chain of the thermosensitive conductive layer tends to form a hydrophilic stretch straight-chain conformation, and the extracellular matrix is pushed away and the cells can be removed from the surface without damaging the integrity of the cell sheet, and the above process is called the cooling and detaching process. Through the cooling and detaching process, the cell sheets on the thermosensitive conductive layer can be harvested without damage.

Figure 5:
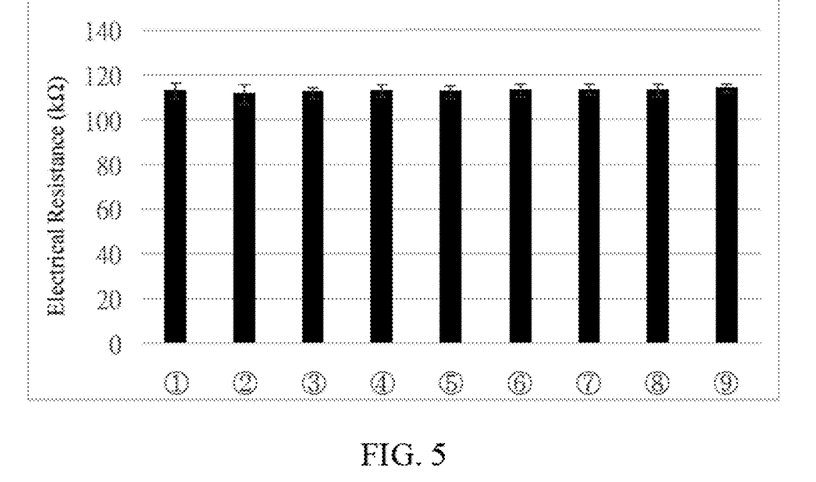
FIG. 5 is a bar graph showing the resistance distribution statistics of the composite elastic thermosensitive conductive membrane prepared in accordance with the method disclosed in the present invention.

FIG. 5 is a bar graph showing the resistance distribution statistics for the composite elastic thermosensitive conductive membrane prepared in accordance with the method disclosed in the present invention. As shown in FIG. 5, nine points randomly selected on the membrane are marked as points ①~⑨ for resistance measurement. According to the measurement result, the average resistance value of each of the nine points ①~⑨ is stably in a range of 100 kΩ up to 120 kΩ and the resistance values of the nine points are in a substantively uniform distribution. The uniformly-distributed surface resistance ensures a uniform electric field generated during electrical stimulation and suitable for bioelectric stimulation applications.

Figure 6:
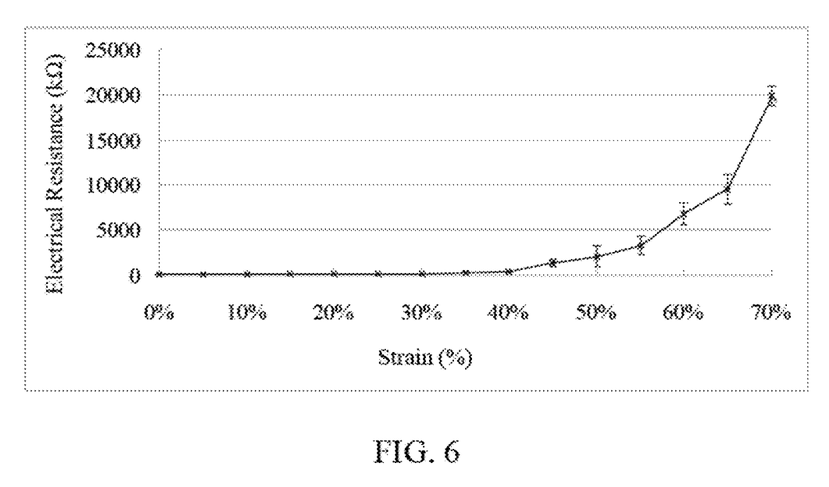
FIG. 6 is a line graph based diagram illustrating the change of the electrical resistance of the composite elastic thermosensitive conductive membrane, in accordance with the present invention, subjected to and in response to different strains.

FIG. 6 is a line graph based diagram illustrating the change of the electrical resistance of the composite elastic thermosensitive conductive membrane, in accordance with the present invention, subjected to and in response to different strains. When the composite elastic thermosensitive conductive membrane is stretched upon subjected to an external tensile force, and it must ensure that the thermosensitive conductive layer is not broken during stretching. The composite elastic thermosensitive conductive membrane is respectively stretched with different selected strains or also known as the stretching ratio, to measure the changes of resistance values under different stretching ratio. According to the measurement results, it can be known that the resistance of the composite elastic thermosensitive conductive membrane slightly increases as the stretching ratio increases. and significantly increases only when the stretching ratio is greater than 40%. As a result, as long as the stretching ratio does not exceed 40%, the composite elastic thermosensitive conductive membrane can be substantively maintained at the status for providing electrical resistance of less than 1000 kΩ.

Figure 7:
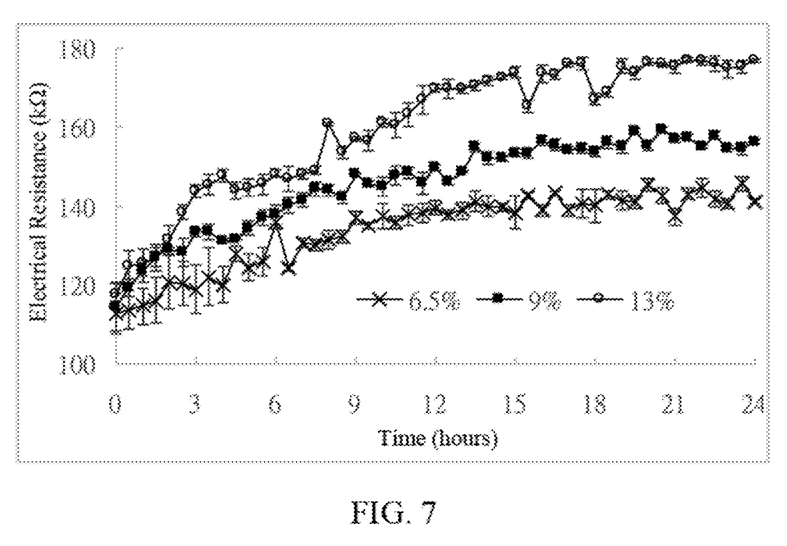
FIG. 7 is a line graph based diagram illustrating the change of resistance of the invented composite elastic thermosensitive conductive membrane during repeated stretching, in accordance with the present invention

FIG. 7 is a line graph based diagram illustrating the change of resistance of the invented composite elastic thermosensitive conductive membrane during repeated stretching, in accordance with the present invention. When the composite elastic thermosensitive conductive membrane is repeatedly stretched, whether thermosensitive conductive layer is broken during stretching and the corresponding change of resistance are necessary test items for checking durability of the composite elastic thermosensitive conductive membrane. In different tests, the composite elastic thermosensitive conductive membrane is repeatedly stretched with the selected stretch ratios of 6.5%, 9% or 13% at a frequency of 0.5 Hz, and the resistance of the composite elastic thermosensitive conductive membrane is measured every half hour. As shown in FIG. 7, when the examination time increases, the resistance of the composite elastic thermosensitive conductive membrane rises slightly, but the thermosensitive conductive layer is not broken, so it can be confirmed that the composite elastic thermosensitive conductive membrane in accordance with the present invention can withstand repeated stretching for a long time, and the reason is that the thermosensitive conductive layer is tightly combined with the PDMS membrane processed by the chemical surface modification, and the composite elastic thermosensitive conductive membrane is reliable in repeated stretching applications.

Furthermore, the micro pores formed on the surface by the chemical surface modification process can enhance the combinational strength between the thermosensitive conductive layer of P(Py-co-NIPAAm) and the elastic membrane of PDMS, and improve the optical properties of the composite membrane, so as to facilitate to use the imaging equipment to observe the cultured tissues or cells. Furthermore, in an actual experiment, the mouse myoblasts (C2C12) are actually cultured on the composite membrane and tested by MTT assay, it is proved that the composite membrane in accordance with the present invention is helpful for the improvement in biological activity of surface cells.

Figure 8:
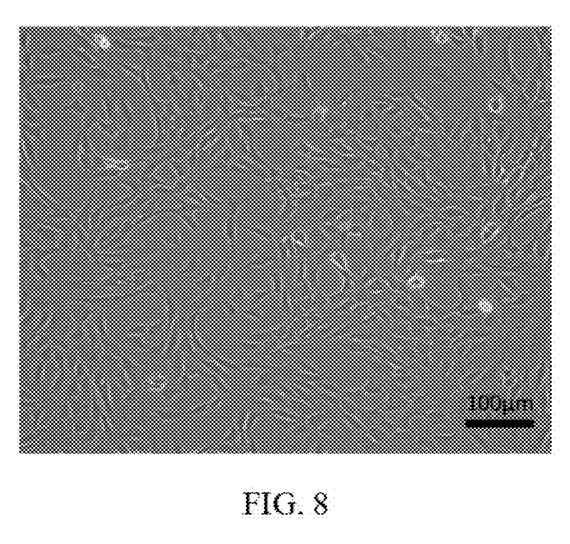
FIG. 8 is an image showing cells cultured on the composite elastic thermosensitive conductive membrane in accordance with the present invention, when being observed by using an inverted microscope with a 10× objective lens.

FIG. 8 is an image showing cells cultured on the composite elastic thermosensitive conductive membrane in accordance with the present invention, when being observed by using an inverted microscope with a 10× objective lens. As mentioned above, the composite membrane in accordance with the present invention is slight dark and transparent which allows 60% to 70% of light pass through. Therefore, when the imaging equipment, such as an inverted microscope, is used to observe the cell tissue cultured on the elastic conductive layer, a clear and identifiable image can be imaged on the imaging equipment.

The P(Py-co-NIPAAm)/PDMS composite elastic thermosensitive conductive membrane proposed in the present invention is able to alert the hydrophilicity of the surface thereof in response to the change of temperature, to achieve the purpose of detachment of cell sheet. By observing the changes in contact angles of the P(Py-co-NIPAAm)/PDMS composite membrane at 37° C. and 4° C., it can determine whether the synthesized copolymer has thermosensitive property.

Figure 9:
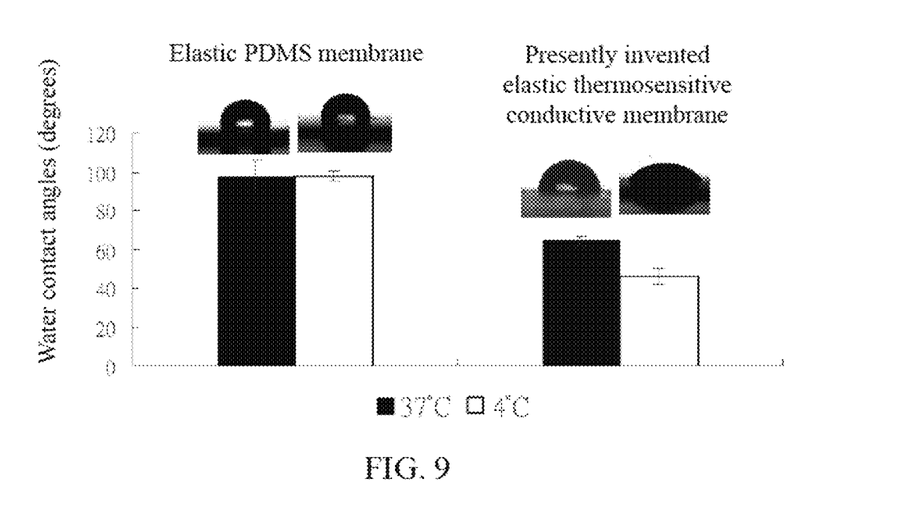
FIG. 9 is a bar graph based diagram illustrating the test results for the water contact angles of the elastic substrate and the elastic thermosensitive conductive membrane in accordance with the present invention at the temperatures of 37° C. and 4° C., respectively.

FIG. 9 is a bar graph based diagram illustrating the test results of the water contact angles of the elastic substrate and the elastic thermosensitive conductive membrane in accordance with the present invention at the temperatures of 37° C. and 4° C., respectively. According to experimental measurement result, it is known that when the temperature drops from 37° C. down to 4° C., the water contact angle of the elastic thermosensitive conductive membrane indeed drops from about 70 degrees down to 42 degrees; in contrast, the water contact angle of the PDMS membrane of the elastic substrate does not change in response to the change of temperature, so the thermosensitive conductive layer formed by the P(Py-co-NIPAAm)/PDMS membrane in accordance with the present invention is indeed thermoresponsive or thermosensitive.

Figure 10:
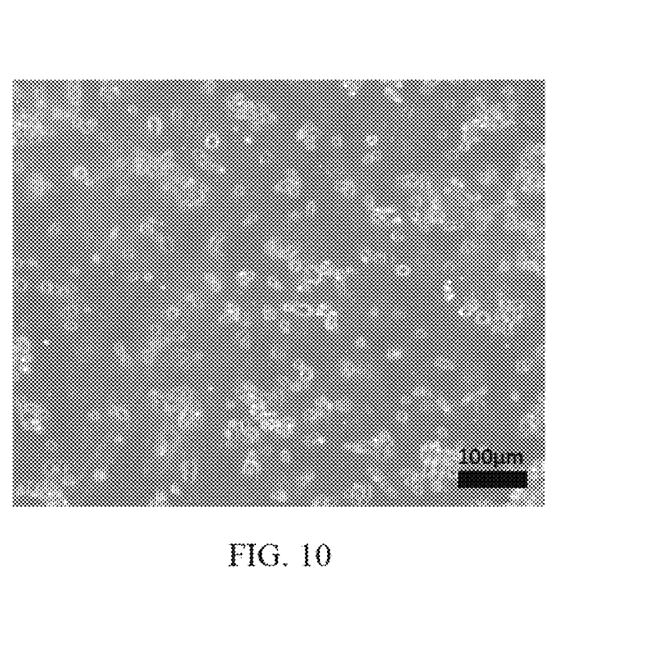
FIG. 10 is a microscopic image showing the cells harvested by using trypsin digestion at 37° C. for 5 minutes, in prior art.
Figure 11:
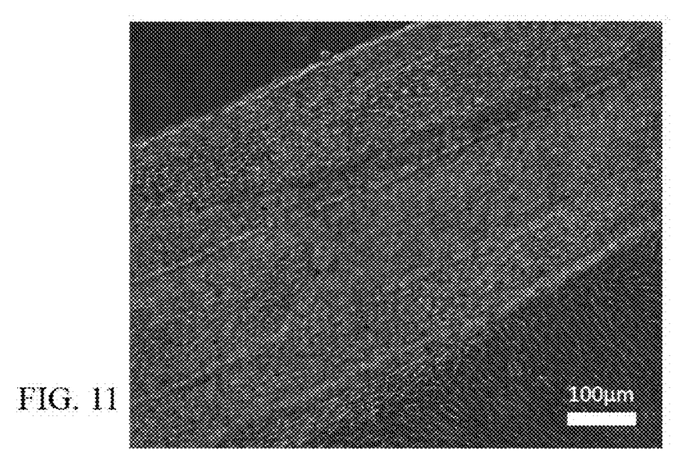
FIG. 11 is a microscopic image showing cells on the P(Py-co-NIPAAm)/PDMS composite membrane harvested as a cell sheet by immersing into PBS solution at 4° C. lasting for 60 minutes, in accordance with the present invention.

FIG. 10 is a microscopic image showing the cell harvested by using trypsin digestion at 37° C. for 5 minutes, in prior art. FIG. 11 is a microscopic image showing the cell sheet harvested by immersing the P(Py-co-NIPAAm)/PDMS composite membrane, where cells are cultured, into PBS solution at 4° C. lasting for 60 minutes, in accordance with the present invention. The P(Py-co-NIPAAm)/PDMS composite membrane in accordance with the present invention can alert a surface property of hydrophilicity in response to the change of temperature, to achieve the purpose of separating cell sheets.

The operation of the cell detaching method proposed by the present invention is quite simple, the whole piece of P(Py-co-NIPAAm)/PDMS composite membrane cultured with cells is immersed in phosphate-buffered saline (PBS) at low temperature for a certain period of time, and then the P(Py-co-NIPAAm)/PDMS composite membrane is rinsed with PBS to automatically peel off the cell sheet. The effect in accordance with the present invention is much better than the conventional cell detaching method based on trypsin digestion mechanism, and the conventional cell detaching method has the problem that the connections between the cells and the tissue structures digested by trypsin are broken, and the extracellular matrix is greatly reduced or even eliminated as well.

The C2C12 cells are cultured on the P(Py-co-NIPAAm)/PDMS membrane, and the cultured C2C12 cells were differentiated when the cells are 90% to 100% full, and a stretching stimulation with the stretch amount of 6.5% is applied to the cultured cells at an implementation frequency of 0.5 Hz for 4 days and 6 hours per day, and the differentiation medium is changed every two days to promote not only cell differentiation and alignment but also parallel myotubes formation. The myotubes arranged in parallel can increase signal transmission between cells. By observing whether the myotube tissues of the cell sheet are retained and maintained in parallel arrangement in the cell sheet processed by the cooling and detaching method in accordance with the present invention, it can verify the effectiveness of the cell detaching method in accordance with the present invention.

The cultured cells are harvested from the culture membrane by using the conventional trypsin method and the cooling and detaching method in accordance with the present invention, respectively. FIG. 10 is a microscopic image showing the individual cells of the cultured cell sheet removed by using trypsin digestion for 5 minutes at 37° C. in prior art. FIG. 11 is a microscopic image showing the cell sheet harvested by immersing the P(Py-co-NIPAAm)/PDMS composite membrane cultured with the cells in the PBS solution at 4° C. lasting for 60 minutes. As shown in FIG. 10, most of the cells processed with trypsin are in the single-cell suspension status; however, as shown in FIG. 11, the cells obtained by the cooling and detaching method with the P(Py-co-NIPAAm)/PDMS membrane in accordance with the present invention is peeled off from the edge in sheet.

Figure 12:
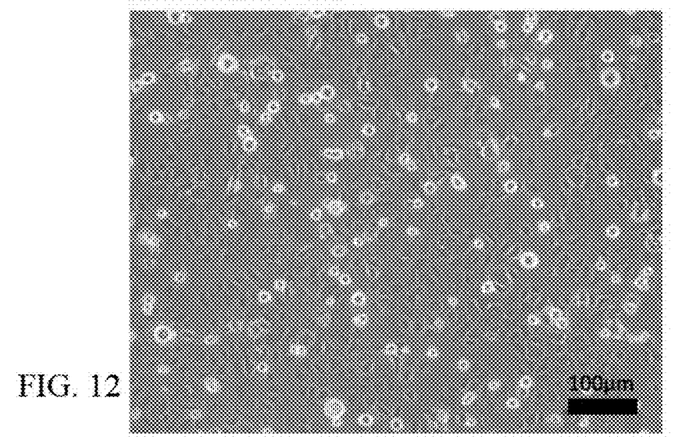
FIG. 12 is a microscopic image showing the cells harvested by trypsin digestion in prior art and replanted in TCPS for one day.
Figure 13:
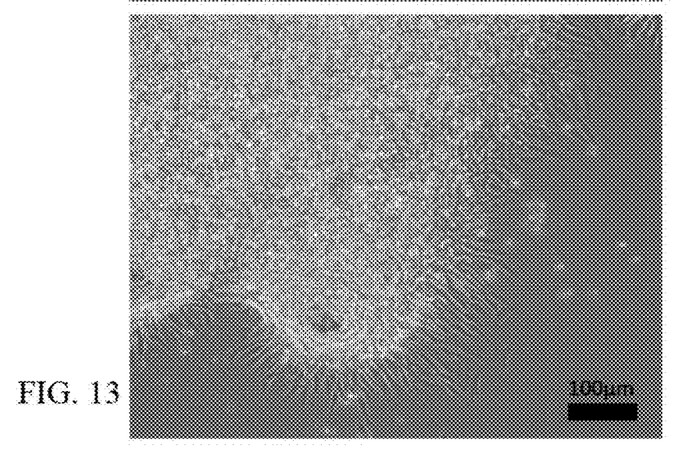
FIG. 13 is a microscopic image showing the cell sheet harvested from the P(Py-co-NIPAAm)/PDMS membrane by using the cooling detaching method in accordance with the present invention and replanted in TCPS for one day.

Next, the obtained cells are replant into a tissue culture polystyrene (TCPS) and culture medium is added in the TCPS, and the cell attachment status is observed with a microscope after one day. FIG. 12 is a microscopic image showing the cells removed by trypsin in prior art and replanted in TCPS for one day. FIG. 13 is a microscopic image showing the cell sheet removed by using the cooling detaching method with the P(Py-co-NIPAAm)/PDMS membrane in accordance with the present invention and replanted in TCPS for one day. As shown in FIG. 13, the edge of the replanted cells, which is removed by using the cooling and detaching method in accordance with the present invention, is well attached with the culture plate; however, some of the replanted cells, which is removed by trypsin in prior art, have died and floated, and most of the cells are single cells, as shown in FIG. 12.

Figure 14:
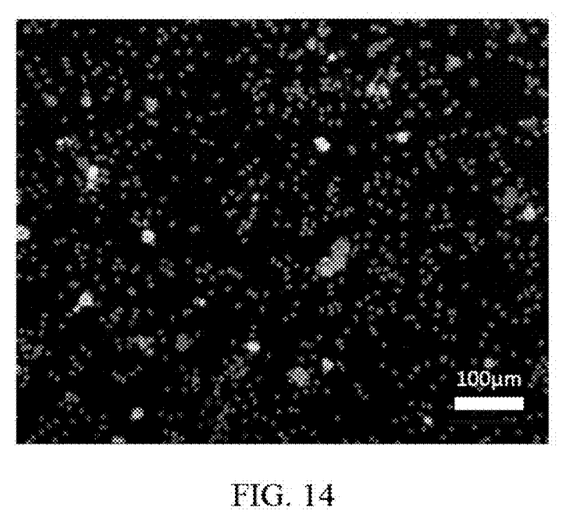
FIG. 14 is a microscopic image showing the replanted cells harvested by trypsin digestion in prior art and illustrated by myosin heavy chain (MHC) immunofluorescence staining.
Figure 15:
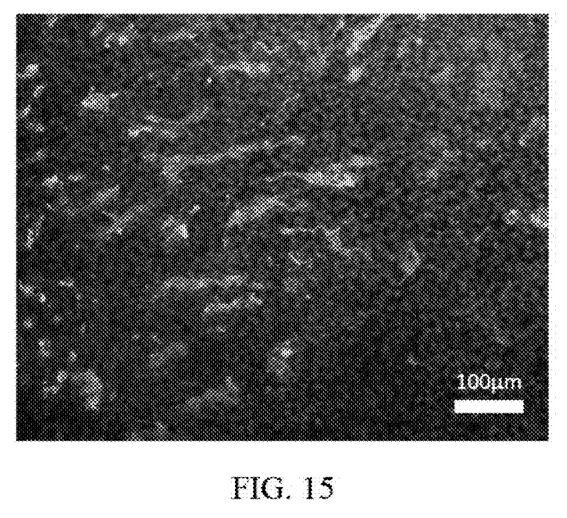
FIG. 15 is a microscopic image showing the replanted cell sheet harvested from the P(Py-co-NIPAAm)/PDMS membrane by using the cooling and detaching method in accordance with the present invention and illustrated by MHC immunofluorescence staining.

After the cells are replanted and attached completely, the MHC immunofluorescence staining is performed the cells to observe whether the cell sheet still retains the arranged myotubes. FIG. 14 is a microscopic image showing the cell sheet removed by trypsin in prior art and processed by MHC immunofluorescence staining. FIG. 15 is a microscopic image showing the cell sheet removed by using the cooling and detaching method with the P(Py-co-NIPAAm)/PDMS membrane in accordance with the present invention and processed by MHC immunofluorescence staining. As shown in FIG. 15, the replanted cell sheet, which is removed by the cooling and detaching method in accordance with the present invention, can retain the original myotubes and the direction of the myotube arrangement is perpendicular to the stretching direction, so the replanted cell sheet clearly expresses shows the arrangement property of myotubes; however, as shown in FIG. 14, the replanted cells, which is removed by using trypsin in prior art, have only few myotubes remained and the remained myotubes are not in arrangement. Therefore, it proves that the cooling and detaching with the P(Py-co-NIPAAm)/PDMS membrane in accordance with the present invention can effectively retain the myotubes contained in the cell sheet without destroying the arrangement of the myotubes.

Figure 16:
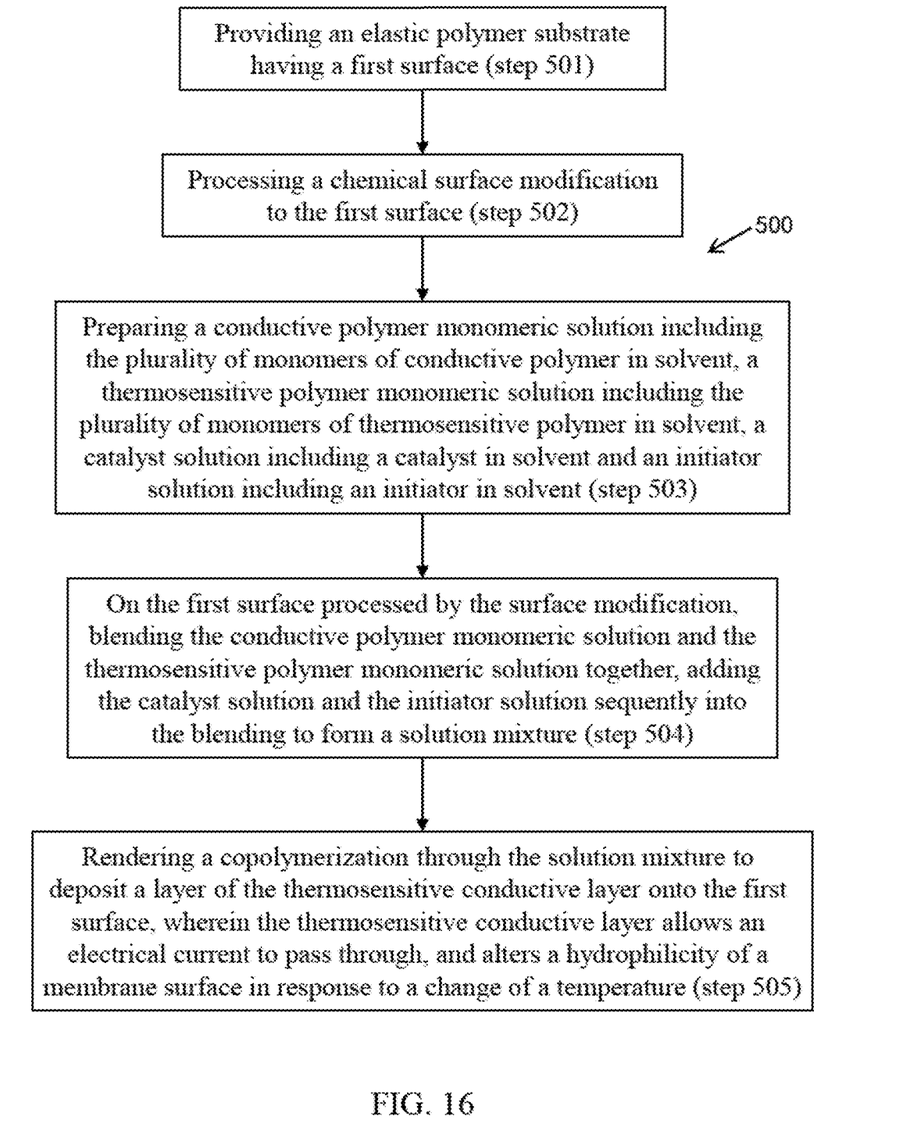
FIG. 16 is a schematic diagram illustrating a composite membrane manufacturing method, according to the present invention.

FIG. 16 is a schematic diagram illustrating a composite membrane manufacturing method, according to the present invention. To sum up, the composite membrane manufacturing method 500 in accordance with the present invention preferably includes the following steps: providing an elastic polymer substrate having a first surface (step 501); processing a chemical surface modification to the first surface (step 502); preparing a conductive polymer monomeric solution including the plurality of monomers of conductive polymer in solvent, a thermosensitive polymer monomeric solution including the plurality of monomers of thermosensitive polymer in solvent, a catalyst solution including a catalyst in solvent and an initiator solution including an initiator in solvent (step 503); on the first surface processed by the surface modification, blending the conductive polymer monomeric solution and the thermosensitive polymer monomeric solution together, adding the catalyst solution and the initiator solution sequently into the blending to form a solution mixture (step 504); and rendering a copolymerization through the solution mixture to deposit a layer of the thermosensitive conductive layer onto the first surface, wherein the thermosensitive conductive layer allows an electrical current to pass through, and alters a hydrophilicity of a membrane surface in response to a change of a temperature (step 505).

There are further embodiments provided as follows.

Embodiment 1: A composite membrane includes: an elastic polymer substrate having a first surface processed by a surface modification; and a thermosensitive conductive layer formed on the first surface by performing a co-polymerization process, allowing an electrical current to pass through, and altering a hydrophilicity of a membrane surface in response to a change of a temperature.

Embodiment 2: The composite membrane as described in Embodiment 1, the thermosensitive conductive layer is stretchable and produces a strain when subjected to a tensile force, and has an electrical resistance in a range of from 50 kiloohms up to 5000 kiloohms within the strain of less than 40%.

Embodiment 3: The composite membrane as described in Embodiment 1, the thermosensitive conductive layer has a surface with a temperature-related wettability, and when the temperature decreases from 37° C. to 4° C., the temperature-related wettability of the membrane surface transforms from a hydrophobic tendency to a hydrophilic tendency and a water contact angle decreases more than 10°.

Embodiment 4: The composite membrane as described in Embodiment 1, the first surface has multiple wrinkled structures, corrugated structures and micro pores that are formed by etching effect resulted from the surface modification to improve surface roughness and to produce activated functional groups.

Embodiment 5: The composite membrane manufacturing method includes: providing an elastic polymer substrate having a first surface; processing the first surface by a surface modification; and copolymerizing a plurality of monomers of conductive polymer and a plurality of monomers of thermosensitive polymer to form a thermosensitive conductive layer on the first surface, wherein the thermosensitive conductive layer allows an electrical current to pass through, and alters a hydrophilicity of a membrane surface in response to a change of a temperature.

Embodiment 6: The composite membrane manufacturing method as described in Embodiment 5, further includes one of steps as follows: preparing a conductive polymer monomeric solution including the plurality of monomers of conductive polymer in solvent, a thermosensitive polymer monomeric solution including the plurality of monomers of thermosensitive polymer in solvent, a catalyst solution including a catalyst in solvent and an initiator solution including an initiator in solvent; on the first surface processed by the surface modification, blending the conductive polymer monomeric solution and the thermosensitive polymer monomeric solution together, adding the catalyst solution and the initiator solution sequently into the blending to form a solution mixture; and rendering a copolymerization through the solution mixture to deposit a layer of the thermosensitive conductive layer onto the first surface.

Embodiment 7: The composite membrane manufacturing method as described in Embodiment 6, the elastic polymer substrate includes material selected from one of a polydimethylsiloxane (PDMS), a polyurethane (PU), a rubber, an elastomer, and a combination thereof.

Embodiment 8: The composite membrane manufacturing method as described in Embodiment 6, the plurality of monomers of conductive polymer are selected from monomers of a polypyrrole, a polycarbazole, a polyacetylene, a poly(3,4-ethylenedioxythiophene) (PEDOT), a polythiophene, a polyaniline, a polyfluorene, a poly(p-phenylene), a polyazulene, a polynaphthalene, a polypyrenes, a polyindole, a polyazepines, a polyphenylene sulfide, and a combination thereof.

Embodiment 9: The composite membrane manufacturing method as described in Embodiment 6, the plurality of monomers of thermosensitive polymer are selected from monomers of a poly(N-isopropylacrylamide) (PNIPAAm), a poly(N,N-diethylacrylamide) (PDEAAM), a poly(N-vinylcaprolactam) (PVCL), a poly(2-isopropyl-2-oxazoline) (PIOZ), a poly(2-carboxyisopropylacrylamide) (PCIPAAm), a poly(N-(L)-(1-hydroxymethyl) propylmethacrylamide) (P(L-HMPMAAm)), poly(vinyl methyl ether) (PVME), and a combination thereof.

Embodiment 10: The composite membrane manufacturing method as described in Embodiment 6, the initiator is selected from one of a metal peroxide, a hydrogen peroxide, an ammonium persulfate (APS), a potassium persulfate (KPS), an organic peroxide, a dialkyl peroxide, a diisopropyl peroxide, a dilauroyl peroxide, a di-tert-butyl peroxide (DTBP), a dicumyl peroxide, an alkyl hydrogen peroxide, a tert-butyl hydroperoxide (TBHP), a tert-amyl hydroperoxide (TAHP), a cumyl hydroperoxide, a diacyl peroxides, acetyl peroxide, a lauroyl peroxide, a benzoyl peroxide, a peroxide esters, an ethyl benzoate peroxide, a tert-butyl peroxypivalate (TBPP), a tert-amyl peroxypivalate (TAPP), an azo compound, a 2,2'-azobis(2-methylpropionitrile), a 1,1'-azobis(cyclohexanecarbonitrile), and a combination thereof.

Embodiment 11: The composite membrane manufacturing method as described in Embodiment 6, the catalyst is selected from one of a N,N,N',N'-tetramethyl-ethane-1,2-diamine (TEMED), a plurality of ionic compounds composed of $Fe^{2+}$, $Cr^{2+}$, $V^{2+}$, $Ti^{3+}$, $Co^{2+}$, $Cu^+$, and a combination thereof.

Embodiment 12: The composite membrane manufacturing method as described in Embodiment 5, wherein the surface modification is a surface treatment process selected from one of an alkaline aqueous solution immersion process, an acidic aqueous solution immersion process, an oxidant solution immersion process, a plasma processing, an ion beam processing, a high energy electromagnetic radiation processing, and a combination thereof.

While the disclosure has been described in terms of what are presently considered to be the most practical and preferred embodiments, it is to be understood that the disclosure need not be limited to the disclosed embodiments. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the present disclosure which is defined by the appended claims.

What is claimed is:

1. A composite membrane, comprising:
   an elastic polymer substrate having a first surface; and
   a thermosensitive conductive copolymer layer formed on the first surface, configured to allow an electrical current to pass through, and having a surface capable of altering a temperature-related wettability in response to a change of a temperature.

2. The composite membrane as claimed in claim 1, wherein the composite membrane is stretchable and produces a strain when subjected to a tensile force, and has an electrical resistance in a range of from 50 kiloohms up to 5000 kiloohms within the strain of less than 40%.

3. The composite membrane as claimed in claim 1, wherein the thermosensitive conductive copolymer layer has the surface with the temperature-related wettability, and when the temperature decreases from 37° C. to 4° C., the temperature-related wettability of the membrane surface transforms from a hydrophobic tendency to a hydrophilic tendency and a water contact angle decreases at least and more than 10°.

4. The composite membrane as claimed in claim 1, wherein the first surface has multiple wrinkled structures, corrugated structures and micro pores that are formed by etching effect resulted from the surface modification to improve surface roughness and to produce activated functional groups.

* * * * *